(12) United States Patent
Serban et al.

(10) Patent No.: US 9,932,449 B2
(45) Date of Patent: Apr. 3, 2018

(54) HYDROGEN SULFIDE SENSOR AND METHOD

(71) Applicant: HONEYWELL ROMANIA S. R. L., Morristown, NJ (US)

(72) Inventors: Bogdan-Catalin Serban, Bucharest (RO); Octavian Buiu, Bucharest (RO); Cornel P. Cobianu, Bucharest (RO); Mihai Brezeanu, Bucharest (RO)

(73) Assignee: Honeywell Romania s.r.l., Morris Plains, NJ (US)

( * ) Notice: Subject to any disclaimer, the term of this patent is extended or adjusted under 35 U.S.C. 154(b) by 310 days.

(21) Appl. No.: 14/791,813

(22) Filed: Jul. 6, 2015

(65) Prior Publication Data

US 2016/0011142 A1     Jan. 14, 2016

(30) Foreign Application Priority Data

Jul. 9, 2014    (EP) .................................. 14176419

(51) Int. Cl.
| | |
|---|---|
| G01N 27/404 | (2006.01) |
| C08J 3/21 | (2006.01) |
| C08J 3/05 | (2006.01) |
| B05D 7/20 | (2006.01) |
| G01N 27/12 | (2006.01) |
| G01N 33/00 | (2006.01) |
| B82Y 15/00 | (2011.01) |

(52) U.S. Cl.
CPC ................. *C08J 3/21* (2013.01); *B05D 7/20* (2013.01); *C08J 3/05* (2013.01); *G01N 27/127* (2013.01); *G01N 27/4045* (2013.01); *G01N 33/0044* (2013.01); *B82Y 15/00* (2013.01); *C08J 2325/06* (2013.01); *C08J 2327/06* (2013.01); *C08J 2331/04* (2013.01); *C08J 2379/02* (2013.01)

(58) Field of Classification Search
CPC ... G01N 27/4045; G01N 33/0044; B05D 7/20
See application file for complete search history.

(56) References Cited

U.S. PATENT DOCUMENTS

| | | | |
|---|---|---|---|
| 6,311,545 B1 * | 11/2001 | Tamaki | ................ G01N 27/12 422/88 |
| 7,318,351 B2 | 1/2008 | Cobianu et al. | |
| 7,695,993 B2 | 4/2010 | Serban et al. | |
| 7,867,552 B2 | 1/2011 | Serban et al. | |
| 2014/0011286 A1 | 1/2014 | Potyrailo et al. | |

OTHER PUBLICATIONS

Liu et al., "A Gold Nanoparticle/polyaniline Nanofiber Sensor for Defecting H2S Impurity in Hydrogen Fuel," Conference Paper PS-13-2 of the 2013 International Conference on Solid State Devices and Materials, Fukuoka, pp. 412-413.*

(Continued)

*Primary Examiner* — Alex Noguerola
(74) *Attorney, Agent, or Firm* — Schwegman Lundberg & Woessner, P.A.

(57) ABSTRACT

A hydrogen sulfide sensor is disclosed. The hydrogen sulfide sensor includes a substrate, a pair of interdigitated electrodes supported by the substrate, and a nanocomposite based sensing layer deposited on the interdigitated electrodes and configured to interact with hydrogen sulfide.

19 Claims, 3 Drawing Sheets

(56) References Cited

OTHER PUBLICATIONS

Liu et al., "Template-Free Deposition of Polyaniline Nanostructures on Solid Substrates with Horizontal Orientation," *Macromolecues*, 44, Mar. 2011, pp. 2212-2219.*

Pramanik et al., "Facile preparation of polyaniline nanofibers modified bentonite nanohybrid for gas sensor application," *RSC Adv.* 2013, 3, 4574-4581.*

"European Application Serial No. 14176419.1, Response filed Oct. 2, 2015 to Extended European Search Report dated Jan. 9, 2015", 24 pgs.

"European Application Serial No. 14176419.1, Extended European Search Report dated Jan. 9, 2015", 4 pgs.

Crowley, Karl, et al., "Fabrication of Polyaniline-Based Gas Sensors Using Piezoelectric Inkjet and Screen Printing for the Detection of Hydrogen Sulfide", *IEEE Sensors Journal*, 10(9), (Sep. 2010), 1419-1426.

De Barros, R. A., et al., "Solvent co-assisted ultrasound technique for the preparation of silver nanowire/polyaniline composite", *Synthetic Metals*, 60(13-14), (Jul. 2010), 1387-1391.

Hosseini, S. Hossein, et al., "Studies of Thermal and Electrical Conductivity Behaviours of Polyaniline and Polypyrrole Blends with Polyvinyl Acetate, Polystyrene and Polyvinyl Chloride", *Iranian Polymer Journal*, 14(3), (2005), 201-209.

Jang, Jyongsik, et al., "Fabrication of Water-Dispersible Polyaniline-Poly(4-styrenesulfonate) Nanoparticles For Inkjet-Printed Chemical-Sensor Applications", *Advanced Materials*, 19(13), (2007), 1772-1775.

Kulkarni, Milind V., et al., "Synthesis and characterization of polyaniline nanofibres by rapid liquid-liquid interfacial polymerization method", *Chemistry & Chemical Technology*, 5(1), (2011), 55-58.

Pandey, Sudhir K., et al., "A review of sensor-based methods for monitoring hydrogen sulfide", *Trends in Analytical Chemistry*, vol. 32, (2012), 87-99.

Sarfaraz, J., et al., "Printed hydrogen sulfide gas sensor on paper substrate based on polyaniline composite", *Thin Solid Films*, 534, (May 2013), 621-628.

Virji, Shabnam, et al., "Polyaniline Nanofiber Composites with Metal Salts: Chemical Sensors for Hydrogen Sulfide", *Small*, 1(6), (Jun. 2005), 624-627.

Virji, Shabnam, et al., "Polyaniline Nanofiber-Metal Salt Composite Materials for Arsine Detection", *Chemistry of Materials*, 21(14), (2009), 3056-3061.

Wang, J, et al., "Sonochemical preparation of nanocomposite of gamma-zirconium phosphate ($\gamma$-ZrP) and $Cu_2O/CuO$ embedded polyaniline", *Solid State Ionics*, 167(3-4), (2004), 425-430.

Zehhaf, A., et al., "Polyaniline/Montmorillonite Nanocomposites Obtained by In Situ Intercalation and Oxidative Polymerization in Cationic Modified-Clay (Sodium, Copper and Iron)", *Journal of Inorganic and Organometallic Polymers and Materials*, 23(6), (2013), 1485-1491.

* cited by examiner

HYDROGEN SULFIDE SENSOR AND METHOD

RELATED APPLICATIONS

This application claims the benefit of priority under 35 U.S.C. Section 119 to European Patent Application Serial No. 14176419.1, filed on Jul. 9, 2014, which application is incorporated herein by reference in its entirety.

BACKGROUND

Hydrogen sulfide sensors can be used in various industries to detect hydrogen sulfide, a toxic, flammable, and corrosive gas. For example, hydrogen sulfide sensors can be used for detecting hydrogen sulfide in the petrochemical industry.

SUMMARY

A hydrogen sulfide sensor is disclosed. The hydrogen sulfide sensor includes a substrate, a pair of interdigitated electrodes supported by the substrate, and a nanocomposite based sensing layer in electrical contact with the interdigitated electrodes and configured to interact with hydrogen sulfide.

In an example, a method of forming a hydrogen sulfide sensor includes dispersing an isolator polymer or a clay in distilled water to form a first dispersion, dispersing, by sonication, synthesized polyaniline nanofibers within the first dispersion to form a second dispersion, suspending, by sonication, a metal salt solution in the second dispersion to form a suspension, and depositing at least a portion of the suspension on a substrate supporting interdigitated electrodes to form a hydrogen sulfide sensor.

DETAILED DESCRIPTION OF THE DRAWINGS

The embodiments of the present disclosure will be described, by way of example only, by reference to the FIGS. 1-3 of the accompanying drawing in which.

DETAILED DESCRIPTION

The present disclosure is directed toward a hydrogen sulfide sensor and a method for making the hydrogen sulfide sensor. The hydrogen sulfide sensor can incorporate a polymer, such as polyaniline, capable of detecting hydrogen sulfide at room temperature as well as elevated temperatures, including, but not limited to about 150° C. to about 250° C. The hydrogen sulfide sensor of the present disclosure can include a sensing layer including polyaniline, a metal salt, such as such a silver (I) salt or a copper (I) salt, and an isolator polymer, such as at least one of polyvinyl acetate, polystyrene, and polyvinyl chloride, or a clay, such as at least one of muscovite, kaolinite, montmorilonite, bentonite, and dickite.

Previous approaches have included conducting-polymer hydrogen sulfide sensors. In such approaches, the sensing mechanism is based on an increase in conductivity of a film of the sensor including polyaniline and a metal salt due to a reaction between the metal salt and hydrogen sulfide, followed by the protonation of the emeraldine free base. The product of this reaction, such as emeraldine salt, is irreversible in the presence of interdigitated electrodes and prevents recovery of the hydrogen sulfide sensor in the presence of hydrogen sulfide. The present disclosure provides a hydrogen sulfide sensor including interdigitated electrodes configured to not react with a metal salt or, so as to provide a reusable hydrogen sulfide sensor. In the present disclosure, a hydrogen sulfur sensor configured to detect hydrogen sulfide on a single occasion includes a disposable sensor, such as a dosimeter. The dosimeter can include metal electrodes configured to not react with a metal salt.

Figure 1:
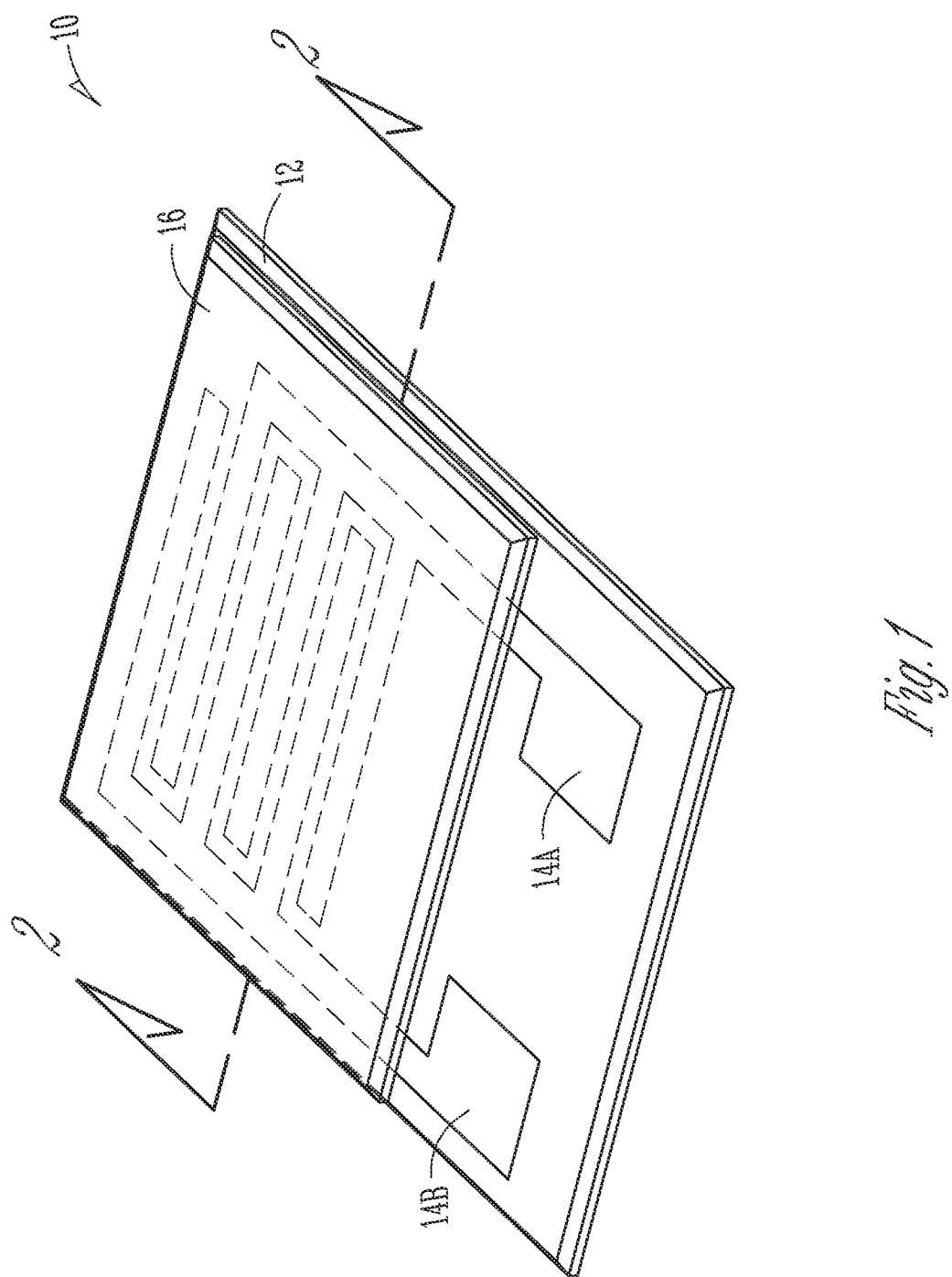
FIG. 1 shows a partial cut-away perspective view of a hydrogen sulfide sensor, in accordance with at least one example.

FIG. 1 shows a partial cut-away perspective view of a hydrogen sulfide sensor 10 (hereinafter also referred to as "sensor 10"), in accordance with at least one example. The sensor 10 can include a substrate 12. The substrate 12 can include at least one of silicon dioxide, silicon, quartz, glass, or the like. In an example, the substrate 12 can be formed of a flexible material such that the substrate 12 can conform to non-planar surfaces. In another example, the substrate 12 is not flexible.

As shown in the example of FIG. 1, the sensor 10 can include interdigitated electrodes (IDEs) 14A, 14B supported by the substrate 12. The IDEs can be supported by the substrate such as be depositing the IDEs on a surface of the substrate. Interdigitated electrodes 14A, 14B include two individually addressable interdigitated comb-like electrode structures. The IDEs 14A, 14B can include carbon, silver, copper, or combination thereof. In an example, the IDEs 14A, 14B can be screen printed on the substrate 12.

As shown in FIG. 1, the sensor 10 can include a nanocomposite based sensing layer 16 (hereinafter also referred to as "sensing layer" 16) configured to interact with hydrogen sulfide. That is, the sensing layer 16 can be in electrical contact with the IDEs 14A, 14B, such that conductivity of the sensor 10 can vary based on the interaction between the sensing layer 16 and the IDEs 14A, 14B. In an example, the sensing layer 16 includes polyaniline. As discussed herein, the polyaniline can be synthesized from o-methoxy aniline or o-ethoxy aniline. The sensing layer 16 includes polyaniline, a metal salt, such as a silver (I) salt or a copper (I) salt, and either a clay or an isolator polymer. The silver (I) salt can include silver (I) acetate. The copper (I) salt can include copper (I) acetate. Silver (I) acetate and copper (I) acetate follow the "Hard Soft Acid Base" (HSAB) rule and are employed because the sulfides yielded by their reaction with $H_2S$ have a low solubility product, which, in turn, leads to increased sensor sensitivity. Examples of isolator polymers include polystyrene, polyvinyl acetate and polyvinyl chloride. Muscovite, kaolinite, montmorilonite, bentonite, and dickite are examples of clays that can be used. In an example, the sensing layer can include about 5 wt % to about 10 wt % isolator polymer or clay and about 5 to about 10% wt % metal salt.

In an example, the sensor 10 can include the polyaniline, copper (I) salt, clay or isolator polymer and carbon IDEs 14A, 14B. In an example, the hydrogen sulfide sensor sensing mechanism is based on the increase in the conductivity of the film containing polyaniline and metal salts due to the reaction between the metal salt and hydrogen sulfide (equation (1)). The product of this reaction is hydrochloric acid (a strong acid), which reacts with base-polyaniline (described by formula (2)) by protonating it. Thus, an emeraldine salt (described by formula (3)) is obtained, which increases of conductivity of the film in the presence of hydrogen sulfide. The increase in conductivity of the film conductivity can be correlated with the concentration of the hydrogen sulfide present.

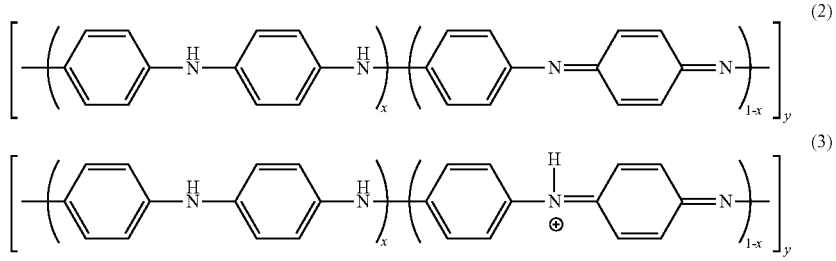

Likewise, low or zero current or conductivity can indicate the lack of hydrogen sulfide present. Similar reactions can take place with a sensor (10) including polyaniline, silver (I) acetate, clay or isolator polymer, and carbon IDEs 14A, 14B. In this case, reaction (1) is replaced with reaction (4):

Figure 2:
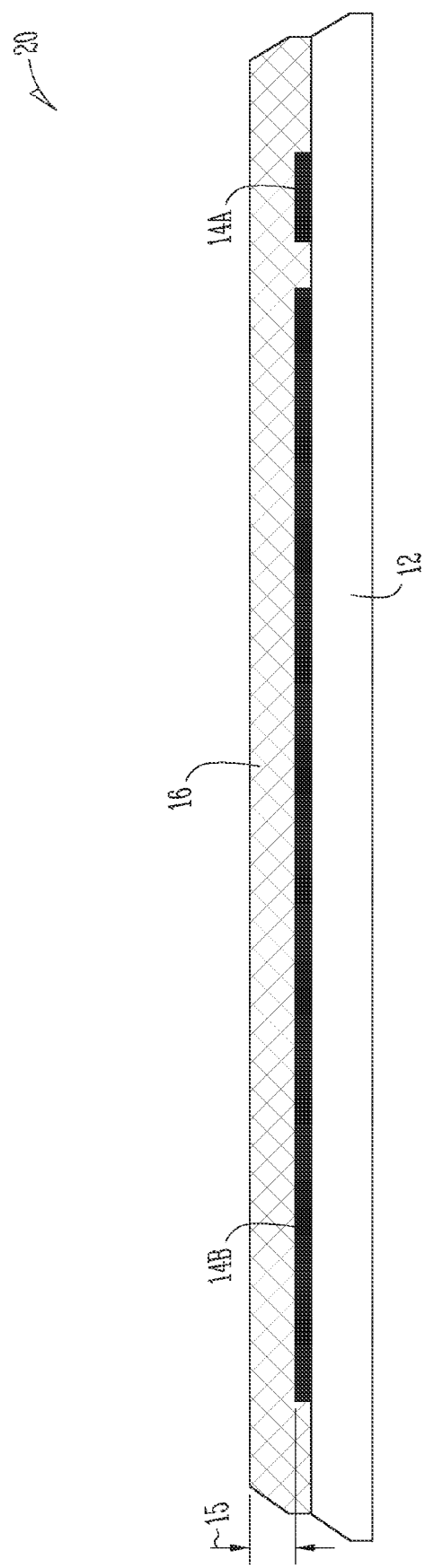
FIG. 2 shows a cross-sectional view of a hydrogen sulfide sensor, in accordance with at least one example.

FIG. 2 shows a cross-sectional view 20 of the hydrogen sulfide sensor 10. The sulfide sensor can include a substrate 12. Substrate 12 can include the materials described above with respect to substrate. Interdigitated electrodes 14A and 14B can be deposited on the substrate 12, such as by a direct printing method. In an example, the sensing layer 16 can be deposited on the IDEs 14A, 14B so as to encompass the IDEs 14A, 14B and form a thin layer above the IDEs 14A, 14B. In an example, a thickness 15 of the layer above the IDEs is about 0.2 μm, 0.4 μm, 0.6 μm, 0.8 μm, 1 μm, 1.2 μm, 1.4 μm, 1.6 μm, 1.8 μm, or 2.0 μm or greater.

In an example, the sensor 10 is configured to detect hydrogen sulfide at room temperature. Room temperature can include about 20° C. to about 23.5° C. Further, the sensor 10, in an example, is configured to detect hydrogen sulfide at elevation temperatures, such as about 150° C. to about 250° C. The sensor 10 of the present disclosure, including the sensing layer described herein, can provide a benefit of sensing hydrogen sulfide at elevated temperatures as compared to sensors only having polyaniline.

Figure 3:
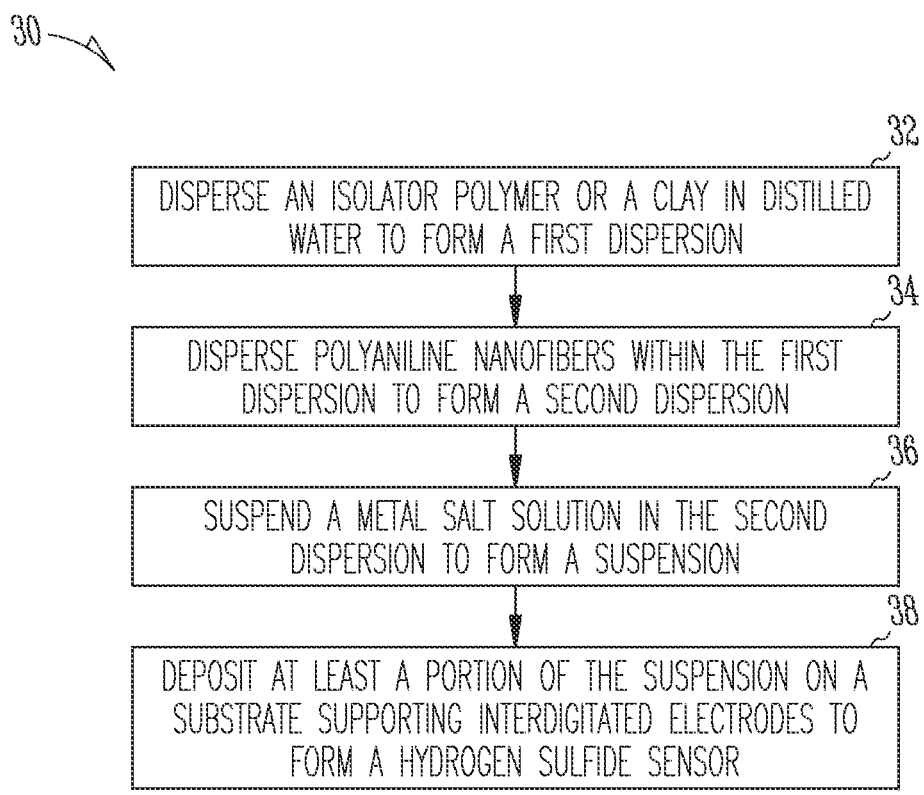
FIG. 3 shows a method of forming a hydrogen sulfide sensor, in accordance with at least one example.

FIG. 3 illustrates a method of forming a hydrogen sulfide sensor 30. At 32, the method includes dispersing either the isolator polymer or the clay in distilled water to form a first dispersion. The isolator polymer can include at least one of polystyrene, polyvinyl acetate, and polyvinyl chloride. Clays can include muscovite, kaolinite, montmorilonite, bentonite, and dickite. In an example, dispersion 32 can include sonication for a predetermined time period. The predetermined time period can range from about 50 hours, to about 60 hours, to about 70 hours, or about 75 hours. In an example, the predetermined time period is about 72 hours.

In an example, the method 30 can include synthesizing polyaniline nanofibers from at least one of o-methoxy aniline and o-ethoxy aniline, such as by interfacial polymerization. The synthesizing can provide synthesized polyaniline nanofibers. At 34, the method includes dispersing, by sonication, the synthesized polyaniline nanofibers within the first dispersion to form a second dispersion. In an example, the polyaniline nanofibers lengths can range from about 200 nm to about 700 nm in length. Sonication can aid in dispersing the polyaniline nanofibers within the first dispersion. In an example, the sonication of the synthesized polyaniline nanofibers can be done for about 15 hours, about 18 hours, about 21 hours, about 24 hours, about 27 hours, or about 30 hours.

The method 30 can include suspending, such as by sonication, a metal salt solution within the second dispersion to form a suspension, at 36. The metal salt solution can include silver (I) acetate or copper (I) acetate. In an example, the sonication of the metal salt solution with the second dispersion can be done for about 15 hours, about 18 hours, about 21 hours, about 24 hours, about 27 hours, or about 30 hours.

At 38, the method can include depositing at least a portion of the suspension on a substrate, such as substrate 12 of FIG. 1, the substrate supporting IDEs, such as being deposited on the substrate, such as by direct printing described herein, to form a hydrogen sulfide sensor, such as sensor 10 of FIG. 1. The hydrogen sulfide sensor form by the method 30 can function as described herein. For example, the hydrogen sulfide sensor can operate at room temperature or elevated temperatures. In an example, the method 30 includes thermally consolidating the sensing layer of the hydrogen sulfide sensor, such as at a temperature at least equal to the ambient temperature during sensor operation. During thermal consolidation, the sensing layer can transform from a gel like, layer obtained during a dropping or spinning process, to a solid state layer to be then used for hydrogen sulfide sensing. In an example, the hydrogen sulfide sensor can irreversibly react in the presence of hydrogen sulfide, such as in the case of a dosimeter.

EXAMPLES

Examples of the present disclosure provide a hydrogen sulfide sensor configured to detect the presence of hydrogen sulfide by an increase in conductivity of a sensing layer.

Example 1 includes subject matter directed toward a hydrogen sulfide sensor, comprising a substrate; a pair of interdigitated electrodes supported by the substrate; and a nanocomposite based sensing layer deposited on the interdigitated electrodes and configured to interact with hydrogen sulfide.

In Example 2, the subject matter of Example 1 can be optionally configured wherein the substrate includes at least one of silicon dioxide, silicon, glass, and quartz.

In Example 3, the subject matter of Examples 1 or 2 can be optionally configured wherein the nanocomposite based composite includes polyaniline and a silver (I) salt or a copper (I) salt.

In Example 4, the subject matter of Examples 1-3 can be optionally configured wherein the nanocomposite based composite includes silver (I) acetate.

In Example 5, the subject matter of Examples 1-4 can be optionally configured wherein the nanocomposite based composite includes copper (I) acetate.

In Example 6, the subject matter of Examples 1-5 can be optionally configured wherein the nanocomposite includes an isolator polymer or a clay.

In Example 7, the subject matter of Examples 1-6 can be optionally configured wherein the nanocomposite includes at least one of polystyrene, polyvinyl acetate, and polyvinyl chloride In Example 8, the subject matter of Examples 1-7 can be optionally configured wherein the nanocomposite includes at least one of muscovite, kaolinite, montmorilonite, bentonite, and dickite.

In Example 9, the subject matter of Examples 1-8 can be optionally configured wherein the hydrogen sulfide sensor is configured to sense hydrogen sulfide from about 150° C. to about 250° C.

Example 10 includes subject matter directed toward a method of forming a hydrogen sulfide sensor, comprising: dispersing an isolator polymer or a clay in distilled water to form a first dispersion; dispersing, by sonication, synthesized polyaniline nanofibers within the first dispersion to form a second dispersion; suspending, by sonication, a metal salt solution in the second dispersion to form a suspension; and depositing at least a portion of the suspension on a substrate supporting interdigitated electrodes to form a hydrogen sulfide sensor.

In Example 11, the subject matter of Examples 1-10 can be optionally configured such that the method further comprises synthesizing the synthesized polyaniline nanofibers from at least one of o-methoxy aniline and o-ethoxy aniline.

In Example 12, the subject matter of Examples 1-11 can be optionally configured wherein suspending the metal salt includes suspending a silver salt or a copper salt for at least 24 hours.

In Example 13, the subject matter of Examples 1-12 can be optionally configured wherein the isolator polymer includes at least one of polystyrene, polyvinyl acetate, polyvinyl chloride.

In Example 14, the subject matter of Examples 1-13 can be optionally configured wherein clay includes at least one of muscovite, kaolinite, montmorilonite, bentonite, and dickite.

In Example 15, the subject matter of Examples 1-14 can be optionally configured such that the method further comprises thermally consolidating the sensing layer to form the hydrogen sulfide sensor.

In Example 16, the subject matter of Examples 1-15 can be optionally configured wherein the interdigitated electrodes are configured to not react with the metal salt.

What is claimed is:

1. A hydrogen sulfide sensor, comprising:
    a substrate;
    a pair of interdigitated electrodes supported by the substrate; and
    a nanocomposite based sensing layer in electrical contact with the interdigitated electrodes and configured to interact with hydrogen sulfide, the nanocomposite including an isolator polymer or a clay.

2. The hydrogen sulfide sensor of claim 1, wherein the substrate includes at least one of silicon dioxide, silicon, glass, and quartz.

3. The hydrogen sulfide sensor of claim 1, wherein the nanocomposite based composite includes polyaniline and a silver (I) salt or a copper (I) salt.

4. The hydrogen sulfide sensor of claim 3, wherein the nanocomposite based composite includes silver acetate.

5. The hydrogen sulfide sensor of claim 3, wherein the nanocomposite based composite includes copper (I) acetate.

6. The hydrogen sulfide sensor of claim 1, wherein the nanocomposite includes at least one of polystyrene, polyvinyl acetate, and polyvinyl chloride.

7. The hydrogen sulfide sensor of claim 1, wherein the nanocomposite includes at least one of muscovite, kaolinite, montmorilonite, bentonite, and dickite.

8. The hydrogen sulfide sensor of claim 1, wherein the hydrogen sulfide sensor is configured to sense hydrogen sulfide from about 150° C. to about 250° C.

9. A method of forming a hydrogen sulfide sensor, comprising:
    dispersing an isolator polymer or a clay in distilled water to form a first dispersion;
    dispersing, by sonication, synthesized polyaniline nanofibers within the first dispersion to form a second dispersion;
    suspending, by sonication, a metal salt solution in the second dispersion to form a suspension; and
    depositing at least a portion of the suspension on a substrate supporting interdigitated electrodes to form a hydrogen sulfide sensor.

10. The method of claim 9, further comprising synthesizing the synthesized polyaniline nanofibers from at least one of o-methoxy aniline and o-ethoxy aniline.

11. The method of claim 9, wherein suspending the metal salt includes suspending a silver (I) salt or a copper (I) salt for at least 24 hours.

12. The method of claim 9, wherein the isolator polymer includes at least one of polystyrene, polyvinyl acetate, polyvinyl chloride.

13. The method of claim 9, wherein clay includes at least one of muscovite, kaolinite, montmorilonite, bentonite, and dickite.

14. The method of claim 9, further comprising thermally consolidating the sensing layer to form the hydrogen sulfide sensor.

15. A method of forming a hydrogen sulfide sensor, comprising:
    dispersing at least one of polystyrene, polyvinyl acetate, polyvinyl chloride or at least one of at least one of muscovite, kaolinite, montmorilonite, bentonite, and dickite clay in distilled water to form a first dispersion;
    dispersing, by sonication, synthesized polyaniline nanofibers within the first dispersion to form a second dispersion;
    suspending, by sonication, one of a silver (I) salt or a copper (I) salt solution in the second dispersion to form a suspension; and
    depositing at least a portion of the suspension on a substrate supporting interdigitated electrodes to form a hydrogen sulfide sensor.

16. The method of claim 15, wherein the polyaniline nanofibers lengths range from about 200 nanometers to about 700 nanometers in length.

17. The method of claim 15, wherein the silver (I) salt is silver (I) acetate and the copper (I) salt is copper (I) acetate.

18. The method of claim 15, further including depositing the interdigitated electrodes onto a surface of the substrate via direct printing.

19. The method of claim 15, wherein the interdigitated electrodes are configured to not react with the metal salt.

\* \* \* \* \*